United States Patent
Kemp et al.

(10) Patent No.: US 9,027,311 B2
(45) Date of Patent: May 12, 2015

(54) STERILISATION SERVICES APPARATUS AND METHOD OF STERILISATION

(75) Inventors: Terry Dean Kemp, Auckland (NZ); Christo Andre De Klerk, Queensland (AU)

(73) Assignee: Mercer Technologies Limited, Auckland (NZ)

(*) Notice: Subject to any disclaimer, the term of this patent is extended or adjusted under 35 U.S.C. 154(b) by 529 days.

(21) Appl. No.: 13/201,169

(22) PCT Filed: Feb. 12, 2010

(86) PCT No.: PCT/NZ2010/000022
§ 371 (c)(1),
(2), (4) Date: Nov. 15, 2011

(87) PCT Pub. No.: WO2010/093266
PCT Pub. Date: Aug. 19, 2010

(65) Prior Publication Data
US 2012/0047850 A1   Mar. 1, 2012

(30) Foreign Application Priority Data

Feb. 13, 2009  (NZ) ........................... 574910
Feb. 13, 2009  (NZ) ........................... 574912

(51) Int. Cl.
*B65B 55/02*   (2006.01)
*A61L 2/07*   (2006.01)
(Continued)

(52) U.S. Cl.
CPC ............... *A61L 2/07* (2013.01); *A61L 2202/14* (2013.01); *A61L 2202/23* (2013.01); *B65B 31/024* (2013.01); *B65B 55/18* (2013.01)

(58) Field of Classification Search
CPC ........ A61L 2/07; B65B 55/18; B65B 31/024; B65B 31/06
USPC .......... 53/403, 405, 407, 408, 425, 434, 167, 53/512; 422/33, 38, 302
See application file for complete search history.

(56) References Cited

U.S. PATENT DOCUMENTS 3,286,430 A * 11/1966 Esty ................................. 53/431
5,534,222 A *  7/1996 Kelbrick et al. ................ 422/33
(Continued)

FOREIGN PATENT DOCUMENTS

EP          0846445        7/2004
WO      WO-02053194        7/2002
(Continued)

OTHER PUBLICATIONS

Mercer Technologies Limited, International Search Report and Written Opinion mailed Jun. 11, 2010, PCT Appln. No. PCT/NZ2010/000022 filed Feb. 12, 2010 (9 pages).

*Primary Examiner* — Andrew M Tecco
(74) *Attorney, Agent, or Firm* — Blakely Sokoloff Taylor & Zafman LLP

(57) ABSTRACT

A method of sterilizing items by placing items to be sterilized into a puncture resistant sealable vapor barrier sterilization bag, performing steam sterilization under pressure via a conduit coupled to the bag while maintaining a heated compensating pressure environment around the exterior of the bag during steam sterilization so as to reduce mechanical stress on the bag and sealing the bag at the completion of sterilization. There is also provided a sterilization services apparatus for sterilizing the contents of a sterilization bag including a pressure compensating compartment having a sealable door that maintains a heated compensating pressure environment around the exterior of a sterilization bag during steam sterilization so as to reduce mechanical stress on the bag.

15 Claims, 10 Drawing Sheets

(51) Int. Cl.
    *B65B 31/02*     (2006.01)
    *B65B 55/18*     (2006.01)

(56) References Cited

U.S. PATENT DOCUMENTS

| | | | | |
|---|---|---|---|---|
| 5,561,964 | A * | 10/1996 | McIntyre et al. | 53/75 |
| 6,622,457 | B2 | 9/2003 | Kurth | |
| 6,977,061 | B2 * | 12/2005 | Lin et al. | 422/33 |
| 7,191,577 | B2 * | 3/2007 | Tamis | 53/425 |
| 2004/0071590 | A1 | 4/2004 | Sawyer | |
| 2009/0032426 | A1 * | 2/2009 | Tateishi et al. | 206/438 |
| 2010/0077701 | A1 * | 4/2010 | Ehmer | 53/425 |

FOREIGN PATENT DOCUMENTS

| | | |
|---|---|---|
| WO | WO-2007055595 | 5/2007 |
| WO | WO 2008119453 A1 * | 10/2008 |

* cited by examiner

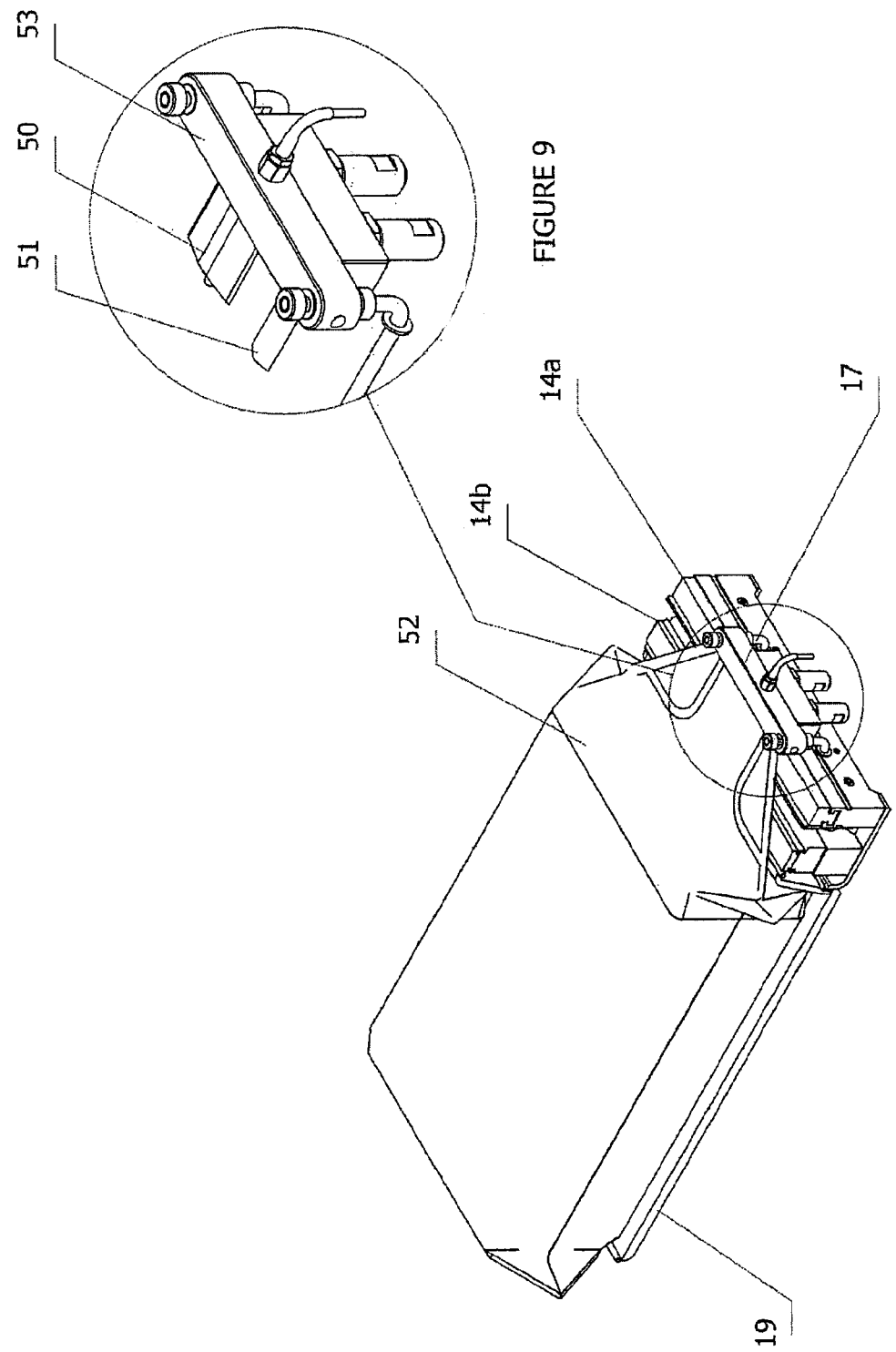

STERILISATION SERVICES APPARATUS AND METHOD OF STERILISATION

CROSS-REFERENCE TO RELATED APPLICATION

The present patent application is a national phase application of International Application No. PCT/NZ2010/000022, filed Feb. 12, 2010.

FIELD OF THE INVENTION

This invention relates to a method of sterilisation and a sterilisation services apparatus. More particularly, although not exclusively, the invention relates to a controlled method and apparatus to facilitate sterilisation and vacuum packing of a sterile load within a package without utilising a conventional steriliser or autoclave.

BACKGROUND TO THE INVENTION

Sterilisation is required for various industries typically health care, laboratory, pharmaceutical and food processing industries. The most common and proven method used for sterilisation is sterilisation by pressurised high temperature steam in a pressure chamber or vessel for a prescribed period of time. Pressurised high temperature steam within a stainless steel pressure chamber is the preferred method for sterilisation of laboratory equipment and in the industrial manufacturing and healthcare sectors.

Various types of sterilisation pressure vessels and autoclave chambers are historically utilised to sterilise such objects, items or products (hereinafter "items"). In all instances the sterilant must make contact with the surface of the items for each item to be sterilised in order to enable sterilisation to occur.

For moist heat sterilisation using steam as the sterilant, it is essential that all surfaces of the items requiring sterilisation are subjected to saturated steam at a predetermined temperature and pressure for a predetermined period of time. Proper steam penetration requires adequate air removal.

Steam is the most widely used agent for sterilisation. In steam sterilisation, the combination of heat and moisture, maintained at a pre-set temperature-pressure-time relationship, coagulates cell protein, efficiently killing the microorganisms. Its economy and lack of toxicity gives steam an advantage over other sterilisation methods. The latent heat available is responsible for the fast destructive power that steam-under-pressure offers. There can be significant variation in steam quality and in order for steam to be effective it should have a dryness fraction of 97% and above.

Each of the multiple or variable types of steam sterilisers are designed to achieve specific sterilisation parameters and all cycles must be validated so that the cycle time and temperature shall reflect the load and packaging material being processed.

At the end of a correct sterilisation process, it is extrapolated that items inside the sterilisation chamber have reached an acceptable probability of sterility. The challenge to end users and steriliser manufacturers has been the variety of loads and varied manner of loading both in respect of how and what items are loaded and positioned in the chamber and how the load may be packaged. The load therefore has a direct impact on the relative efficacy of air removal from the chamber and the efficacy of the steam on the load and addressing and resolving all these variables is still a matter under debate.

In the medical environment, it is necessary that all medical items (equipment and materials) utilised for the treatment of patients are inherently safe for use so that the chance of spreading diseases is kept as low as possible. Hospital acquired infection is clearly the last thing either a patient or the hospital wants.

The challenge therefore is that a steriliser operator must minimise risk and make sure that the steriliser and sterilisation cycle selected for use is suitable for the intended purpose. Sterilisation is a controlled and monitored action and due to these complexities and the requirement to achieve the desired Sterility Assurance Level, international standards have been published; typically ISO 17665 focussing on the effective validation of the sterilisation of loads in a consistent, reproducible and recordable manner and ISO 14937 focussing on the general requirements for characterisation of a sterilisation agent and the development, validation and routine control of a sterilisation process.

An unavoidable problem that faces sterilisation practitioners is that the air in the room where the steriliser is installed contains airborne particles, which may carry microorganisms. Accordingly, when the sterile load is taken out of the steriliser, it may be contaminated again. Additionally sterile goods may be stored for quite some time before they are used. Moreover, they are transported through the hospital to the place they are to be used. It thus is probable that terminally sterile loads/items will become re-contaminated by the time they are used.

Consequently the items must be put in packaging to prevent recontamination after sterilisation. To minimise recontamination and augment the logistics and materials handling expediency of the sterilisation process, the item(s) are usually pre-packaged. The packaging heretofore typically include a fabric barrier typically, muslin wraps, various paper wraps and non-woven wraps, or alternatively laminated film pouches or sterilisation containers. The wraps are typically secured by autoclavable tape which may become detached during processing or in the handling of a package leading to rejection of the package. An important feature of fabric is its "breathability" or the ability of the fabric construction to allow the passage of air and water vapour i.e. steam. Current practices where breathable packaging is required to allow the passage of the sterilant (water vapour/steam) in and out of the package during the sterilisation process places huge demands on the breathable packaging at the conclusion of the sterilisation process to then act as a viral and liquid barrier to ensure impervious protection of the terminally sterile load. The sterilised package should be constructed so that it may be easily opened without the packaging contaminating the contents.

Traditional sterilisation cycles may require up to 20 minutes of air-removal from the chamber and packages and pre-heating of the load(s). Then sterilant is introduced until the correct sterilisation parameters of pressure and temperature have been established; to commence the sterilisation time duration (typically 3.5-5 minutes @ 134 degrees Celsius of steam penetration to facilitate sterilisation). Finally 20-40 minutes of vacuum drying to remove the condensate from the chamber and packages. This results in relatively long sterilisation cycles with limited flexibility.

Sterile services technicians must have an understanding of how to properly select and apply the correct wrap(s) for the sterilisation method chosen. Technicians are also responsible for quality assurance issues. They must assemble each package with care, being observant not to tear or damage the wrap.

Each package is uniquely organised, depending upon content, to promote the sterilisation process. Special attention must also be given to how the steriliser is loaded. After sterilisation the breathable packaging should provide an effective microbial barrier for immediate use of the sterile items or facilitate a shelf life.

It is essential that a packaging system with its content meet the requirements in terms of sterility maintenance and protection of its contents. That is why any packaging should be validated in combination with the actual load and the sterilisation process used.

It is clear to those skilled in the art of sterilisation of an item(s) in a consistent, reproducible and recordable manner, that this goal is made virtually impossible due to the multiple variables faced by sterilisation practitioners daily predominantly as a result of current technology and processes available to sterilisation practitioners.

The applicants prior application published as WO2007/055595 discloses a sterilisation method and apparatus in which items to be sterilised may be sterilised within a plastic bag whilst the exterior of the sterilisation bag is maintained at atmospheric pressure. Whilst effective, maintaining the exterior of the sterilisation bag at atmospheric pressure puts mechanical demands upon the sterilisation bag as it is evacuated and pressurised and may not optimise the flow of fluid into, within and out of the bag. The disclosure of this application is hereby incorporated by reference.

It is the object of the invention to provide an improved sterilisation method and sterilisation services apparatus or to at least provide the public with a useful choice.

SUMMARY OF THE INVENTION

According to one broad aspect of the invention there is provided a method of sterilising items including the steps of:
a. placing items to be sterilised into a puncture resistant sealable vapour barrier sterilisation bag;
b. performing steam sterilisation under pressure via a conduit coupled to the bag whilst maintaining a compensating pressure environment around the exterior of the bag during steam sterilisation so as to reduce mechanical stress on the bag; and
c. sealing the bag at the completion of sterilisation.

The sterilisation bag preferably has a large opening for receiving items to be sterilised (preferably contained within a perforated cage) which may be sealed before performing sterilisation and a second opening for allowing the ingress and egress of fluids into and out of the bag. In a further embodiment one or more additional openings may also be provided connected to a channel into the bag so that circulation of fluid within the bag may be facilitated by supplying fluid via one opening and removing it via the other. At the end of a sterilisation process the second (and third if applicable) openings may be sealed.

The sterilisation bag is preferably evacuated before a sterilisation process and the pressure around the bag is preferably reduced below atmospheric pressure to facilitate effective evacuation of the bag. During steam sterilisation the pressure around the bag is maintained above atmospheric pressure to reduce mechanical stress on the bag. During the sterilisation cycle an external heat source (heated plates) may be applied around the bag and in contact with the walls of the bag to assist the drying of the sterile items.

According to a further aspect of the invention there is provided a sterilisation services apparatus for sterilising the contents of a sterilisation bag including:
a. a pressure compensating compartment having a sealable door that maintains a compensating pressure environment around the exterior of a sterilisation bag during steam sterilisation so as to reduce mechanical stress on the bag;
b. a fluid conduit adapted to couple to an opening of a sterilisation bag during sterilisation within the pressure compensating compartment;
c. a steam generator to supply steam to the bag via the conduit;
d. a bag sealing unit to seal the opening of the sterilisation bag, and
e. a vacuum pump for evacuating a sterilisation bag via the conduit prior to steam sterilisation.

The sterilisation services apparatus may include heated plates within the compensating pressure vessel to heat the exterior of a sterilisation bag. Air may be introduced into the sterilisation bag to facilitate drying of items within a bag.

The sterilisation services apparatus may include a clamp to form a sealed connection between each conduit and each opening in a sterilisation bag. A heat sealing bar and anvil may be provided to seal the openings in a sterilisation bag when sterilisation has been completed.

BRIEF DESCRIPTION OF THE DRAWINGS

The invention will now be described by way of example with reference to the accompanying drawings in which;

FIG. 8 shows a perspective view of the packaging and the loading tray-drawer according to an alternative embodiment, FIG. 9 shows an enlarged view of the snorkel arrangement employed in the embodiment in FIG. 8.

DETAILED DESCRIPTION OF A PREFERRED EMBODIMENT OF THE INVENTION

Figure 1:
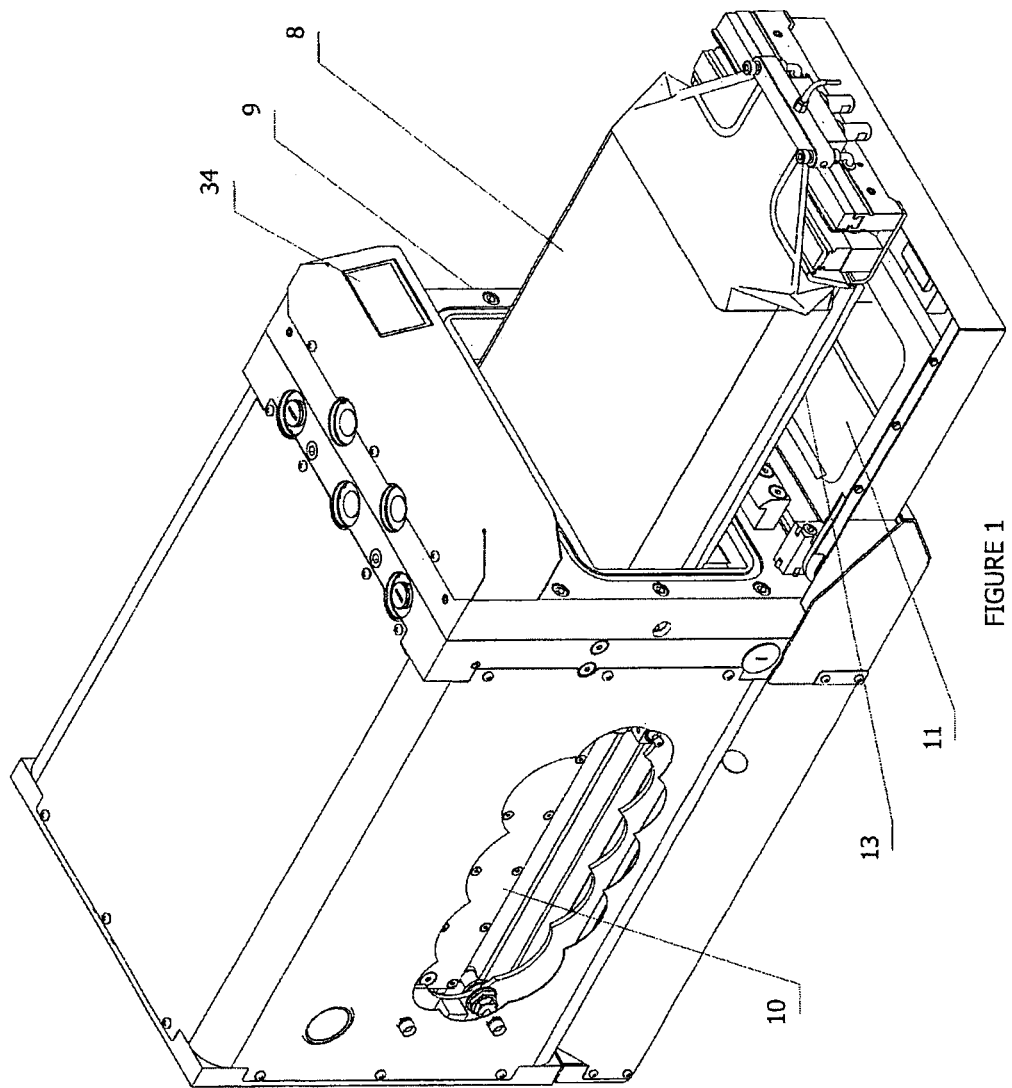
FIG. 1 is a perspective view of a sterilisation services apparatus and a sterilisation bag containing an item or items to be sterilised, the bag being shown in place on a loading tray and drawer arrangement

In response to the challenges encountered by those of skill in the art, from the following description it will be evident that the requirements listed below are desirable:

Enabling Sterilisation

The packaging will allow air that is in the packaging to be evacuated and the sterilant or sterilising agent to be introduced to reach all surfaces of its content (items) via a conduit (snorkel) communicating with an opening (mouth).

Compatible with the Sterilisation Process

The combination of the apparatus and packaging will be able to withstand the conditions that occur during the sterilisation process such as pressure changes, high temperature and humidity.

Ensure Product Integrity and Patient Safety

The sterilisation bag/sterilisation process will not affect the item(s) in any other way, which may affect the quality of the items) or which might endanger the patient or process on which the sterile item(s) will be used, subject to the item(s) to be processed being rated for the sterilisation temperature and pressure.

Maintaining Sterility

After taking the sealed and vacuum packed sterile load/item(s) out of the apparatus it/they will remain sterile during handling, transportation and storage until use, whilst package seal integrity is intact.

Packaging Authentication

Authentication of the packaging prior to sterilisation of item(s) is desirable to ensure an authenticated and validated sterilisation bag is derived from tested and approved film to facilitate the most appropriate functionality with respect to sterilisation process, sealing integrity, handling, transportation and shelf-life.

Tracking and Traceability

The apparatus and packing may desirably process individual loads/trays with each load/tray incorporating a unique identification code written to a RFID tag (attached to the load) and captured in a database to facilitate data logging of process parameters per individual package and to facilitate full tracking and traceability of individual loads throughout its life-cycle.

Indicator

Transparent sealed packaging to facilitate visual verification of sterilisation process indicators.

Facilitate Aseptic Opening and Presentation

When opening a sealed vacuum packed sterile load/item(s), the packaging will facilitate aseptic opening and presentation.

This implies:
  simple opening when removing the sterile load/items from the packaging, package opening will facilitate direct access to the sterile load within the interior of the packaging, the design incorporates an autoclavable perforated basket with lid (preferably of stainless steel mesh construction or similar) that the item(s) are placed in prior to insertion into the packaging (plastic bag). Optionally the basket may be wrapped in a porous fabric/wrap to, further enhance aseptic release of the load in theatre or sterile zone.

Visible Indication that Packaged has been Opened or Breached

Subjecting the package to a vacuum state whence sealed after load sterility is achieved enables immediate visible indication of package vacuum loss due to either a fault of seal integrity loss, package integrity breach or package opening under normal controlled aseptic opening of terminally sterile package. In the event that the package has lost its vacuum as a result of a failure the package may be immediately be deemed contaminated and no longer sterile.

Figure 2:
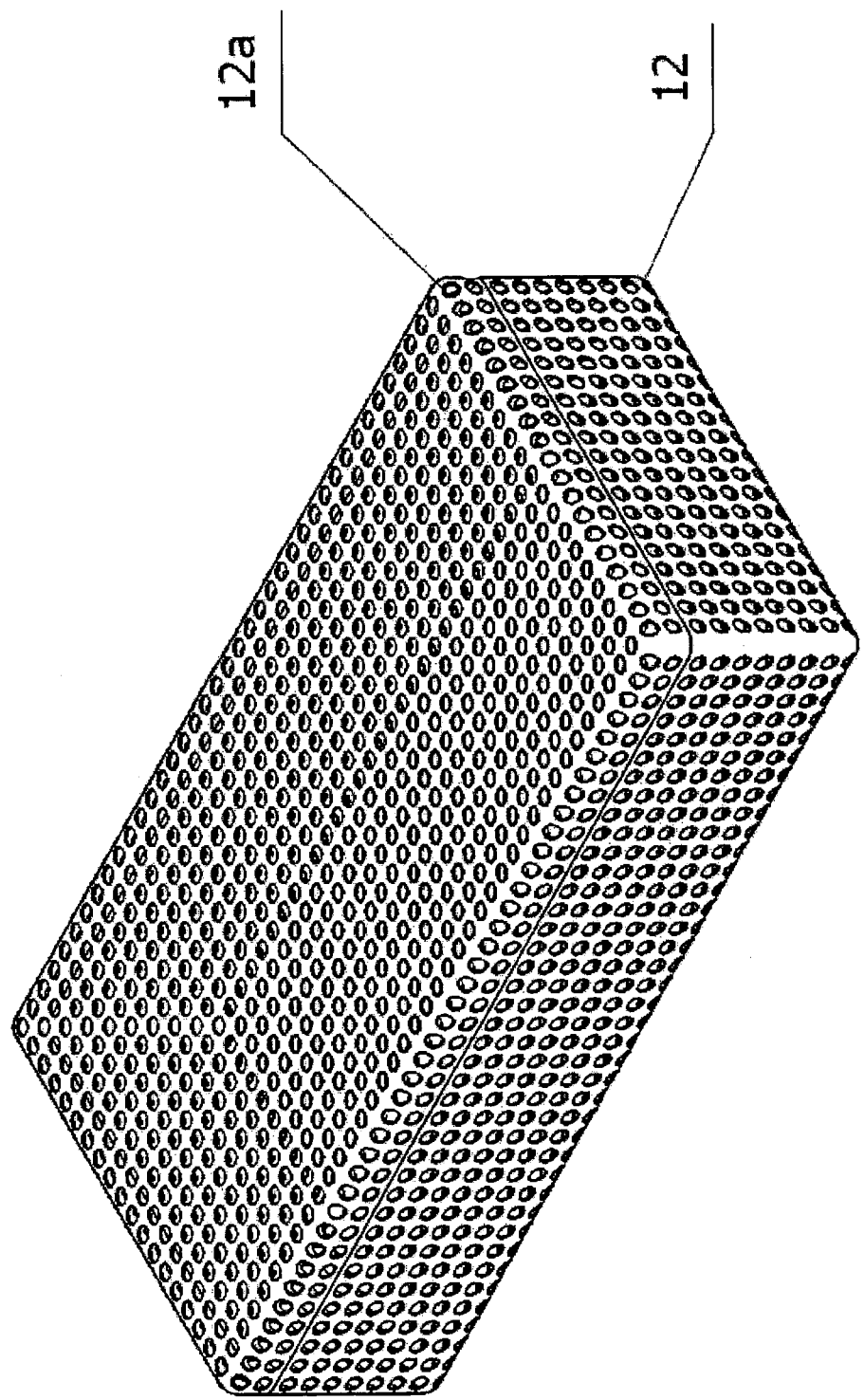
FIG. 2 is a perspective view of a reusable autoclavable basket with a lid to be invested into a sterilisation bag.

The sterilisation services apparatus 9 in one embodiment shown in FIG. 1 is seen to include a pressure compensating compartment 10 including a loading processing tray 13 (capable of interlocking in the pressure compensating compartment 10 when the door 11 is in the closed position) into which is placed a plastic sterilisation bag 8 (packaging), containing the load/basket of item(s) 12 (see FIG. 2) to be processed, The reusable autoclavable basket 12 in the preferred form is a perforated basket with lid 12a (see FIG. 2) is dimensioned to be inserted into the packaging 8. The basket 12 serves a number of purposes—it:
  acts as a carrier basket for the many varied load/items to be sterilised,
  facilitates ease of loading and preferably results in uniform or standardised load packaging,
  enhances the penetration of the sterilant to the items in the basket due to the perforated design,
  assists the removal of the sterilant at the end of the sterilisation cycle,
  ensures and retains a shape for the packaging at the end of the cycle when the sterile load is subjected to a vacuum and sealed and minimises the probability of the load (sharp items) coming into contact with the packaging,
  facilitates a uniform shape for ease of stacking for storage and transportation and general handling.

With correct loading of the load/items in the basket 12 there will potentially be less harm and damage to the load/items during the entire materials handling/logistics cycle e.g. in a hospital environment from the sterile department to theatre and back.

The basket 12 will preferably be of a form that ensures the packaging 8 is not damaged by sharp instruments during the whole vacuum-sealed life cycle of the sterile load.

When the packaging 8 is loaded onto the processing tray 13 of the compensator 10 it is correctly positioned by the door 11 when closed. The processing tray 13 is fitted with part of a clamp 14a (see FIG. 3) and sealing anvil 14b and process snorkel arrangement 17 (see FIG. 4) including a conduit 17a for conveying fluids to and from the bag.

The packaging 8 has an open mouth 7, opposing sides of which will be laid over and under the conduit 17a. Once the packaging 8 is correctly positioned and the mouth 7 opening is routed over and under the conduit 17a and across the clamp 14a and sealing anvil 14b. Then processing basket 12 is ready to positioned in the pressure compensating compartment 10 (compensator) and the door 11 closed and interlocked in place and the sterilisation process can take place.

The sterilisation services apparatus according to one embodiment is envisaged to accommodate a load containing one basket 12 of half a sterilising unit [½StU=30 cm×15 cm×60 cm (W×H×L)] per apparatus. This is by way of example and the invention is not limited to this standard size.

Figure 6:
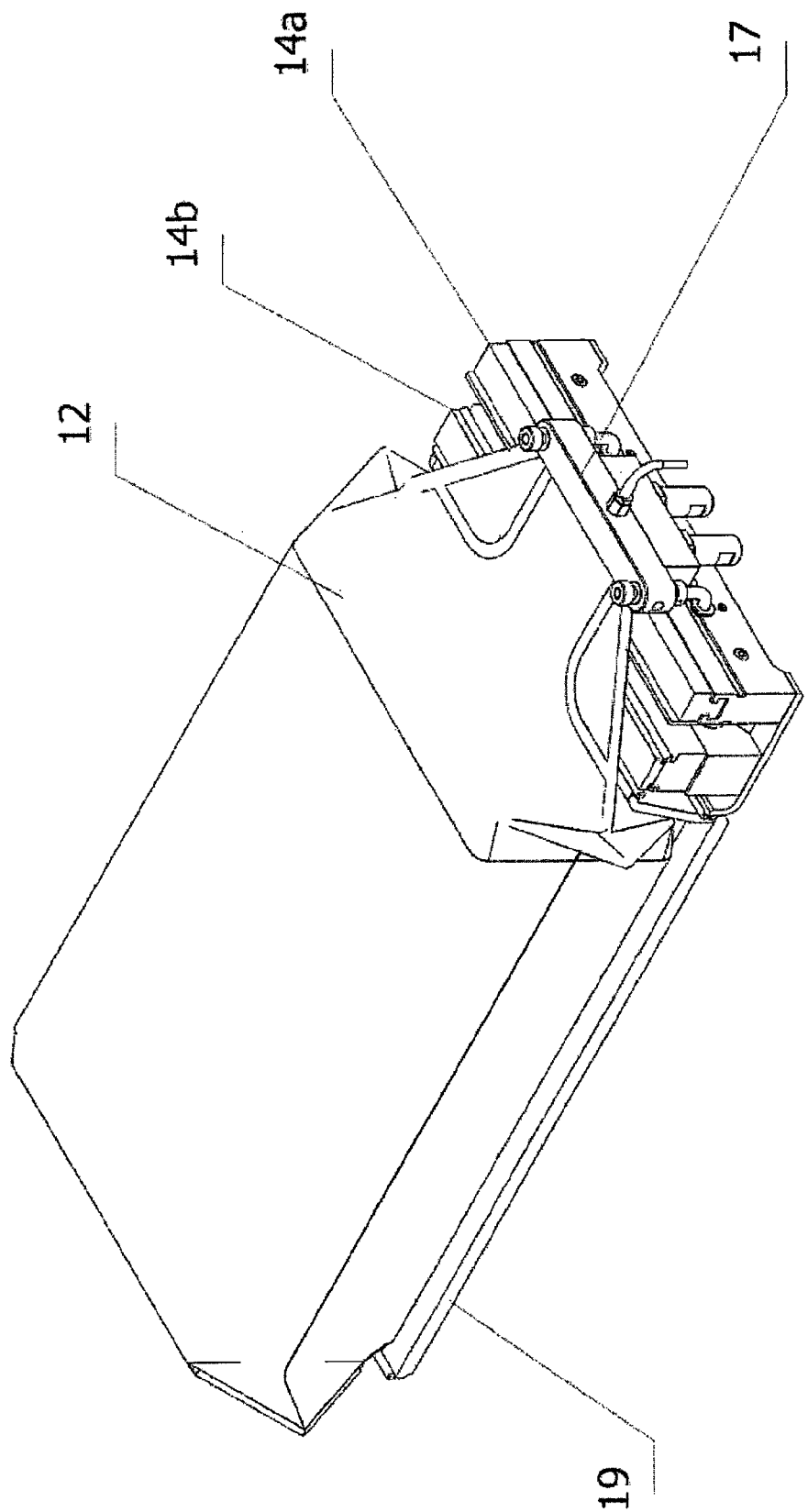
FIG. 6 is a perspective view of the packaging and the drawer loading tray, part of which has been removed in the interests of clarity.

The compensator 10 of apparatus 9 contains a heating plate 20. The combination of the processing tray base-members 19 (see FIG. 6) and the heating plate 20 in the compensator 10 will ensure that contact is made with the length and breadth of the bottom of the package 8 as due to the positive pressure within the package the package will be inflated onto the heating plate and side and top heating plates 21b surrounding the exterior of the package, resulting in the direct heating of any condensation within the package that may settle in the bottom, sides or roof of the package. In addition the heating plates 20 and 21b may assist during the drying phase as it will apply direct heat to the package whilst the vacuum is applied to dry the contents of the package.

Figure 5:
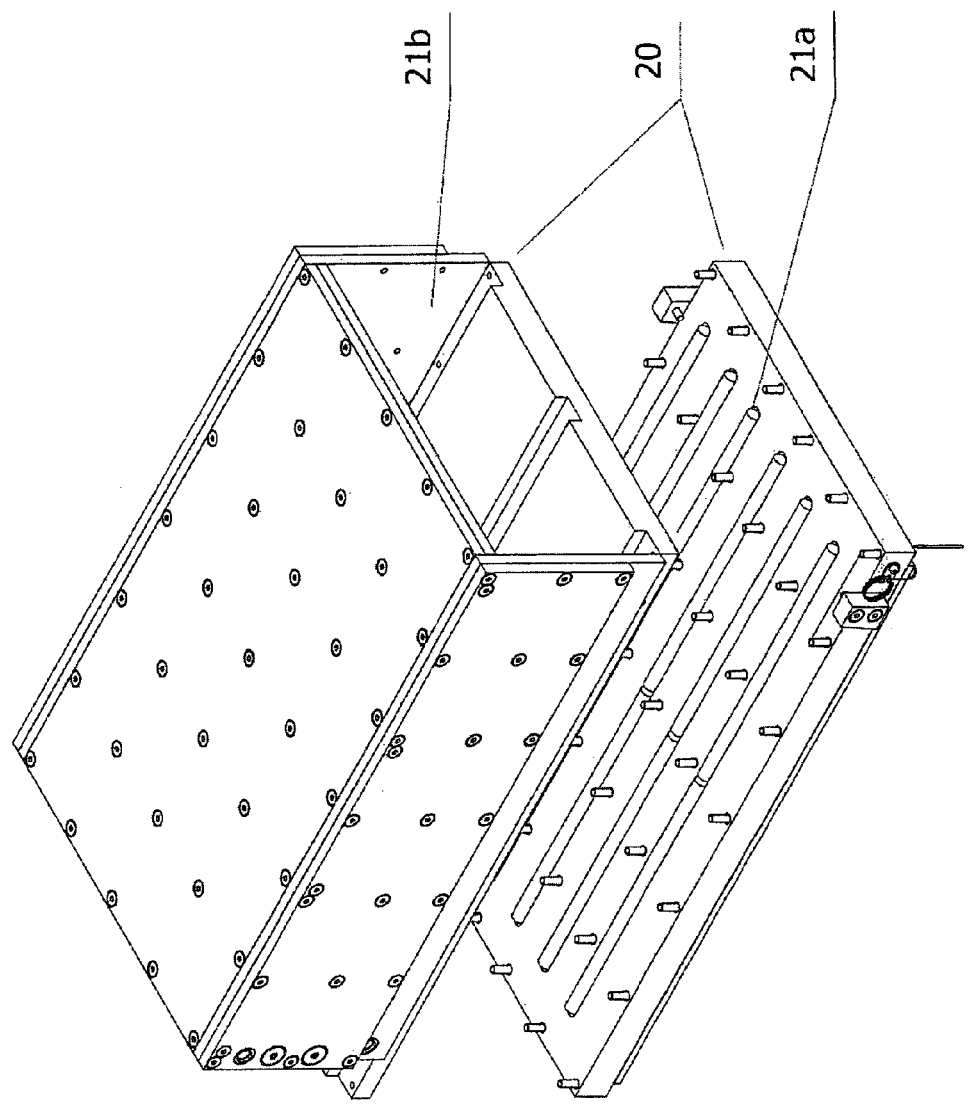
FIG. 5 is a perspective view of a heating plate for the base of the packaging and side and top heating plates to heat the exterior of the package within the pressure compensation vessel.

The heating plate 20 in the compensator 10 (see FIG. 3) contains, in one form, electrical elements 21a (see FIG. 5).

A clamp 22a and seal bar 22b arrangement is housed in the compensator 10 on one side of the compensator above the door 11 opening.

Figure 7:
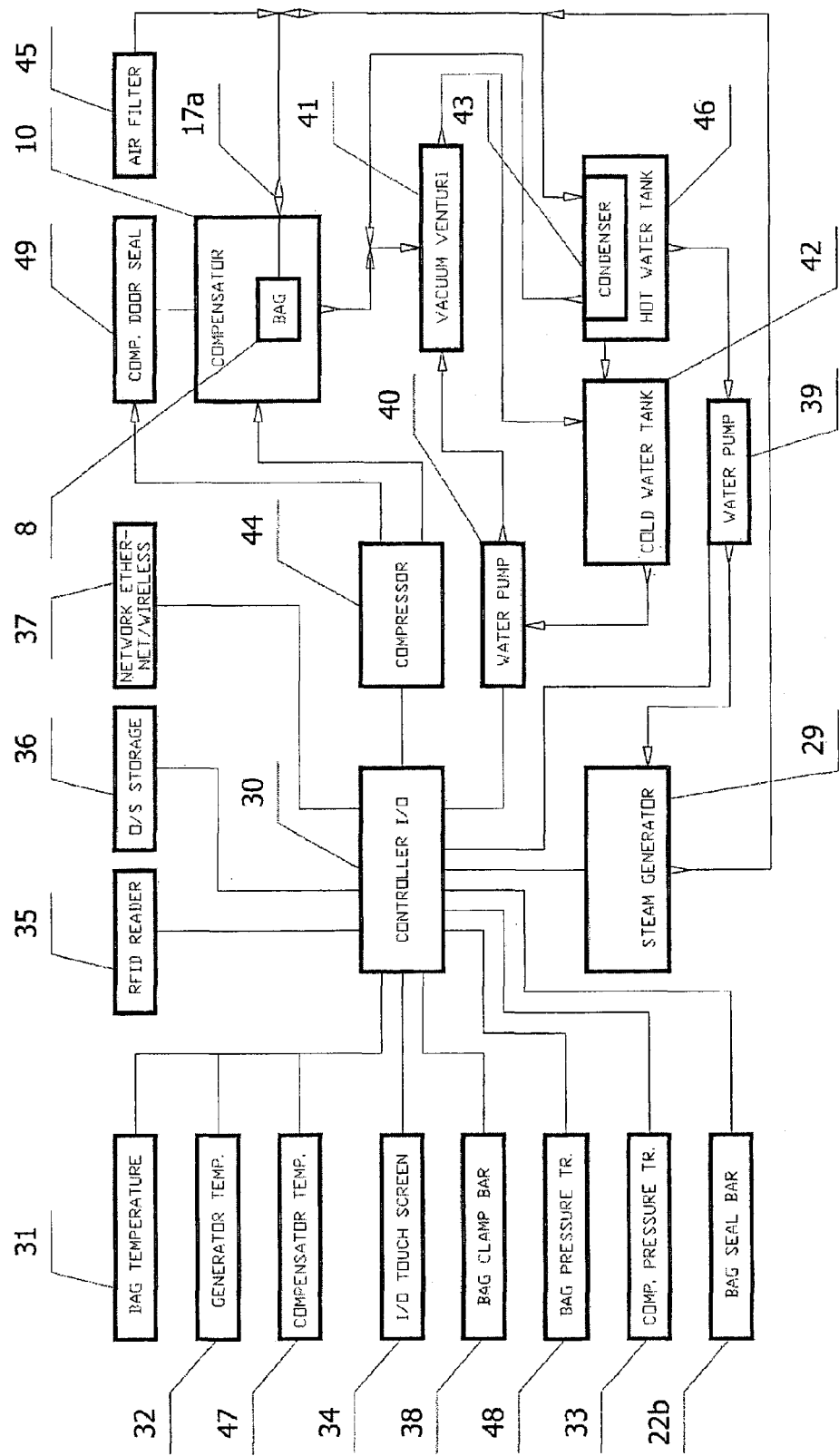
FIG. 7 is a schematic diagram of the electric and fluid system of the embodiment shown in FIGS. 1 to 6.
Figure 10:
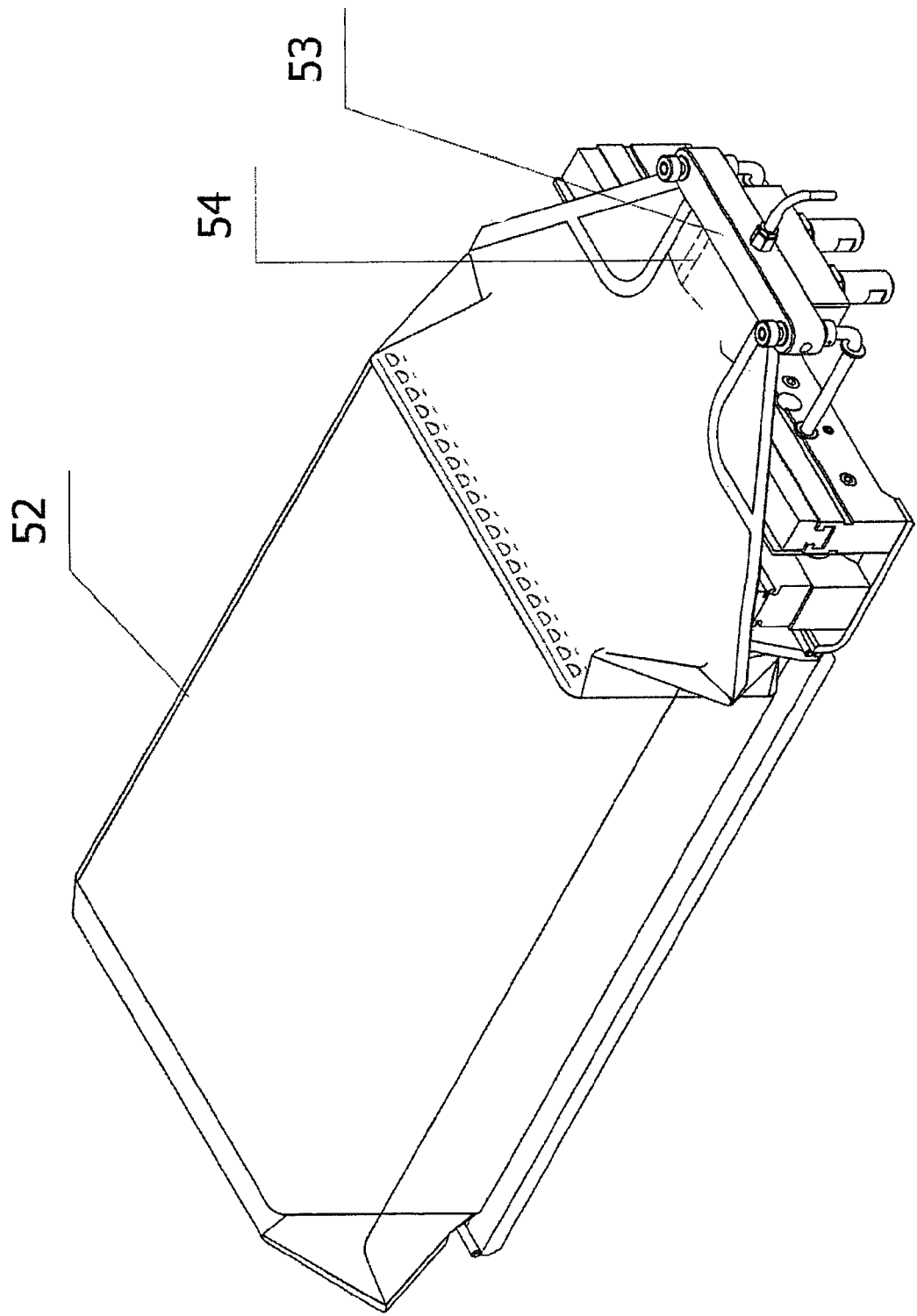
FIG. 10 shows a perspective view of the snorkel of the embodiments shown in FIGS. 8 and 9 engaged with the bag.

Referring now to FIG. 7 a schematic diagram of the electrical and fluid system of the embodiment shown in FIGS. 1 to 6 is shown. The sterilisation services apparatus 9 includes a controller 30 which receives information from sensors and inputs from input devices and controls the operation of the sterilisation services apparatus. A temperature sensor 31 provides controller 30 with information as to the temperature of fluids supplied to the sterilisation bag via a nozzle 17a. Sensor 32 provides controller 30 with information as to the temperature of heating plates 20 and 21b. Pressure sensor 33 provides controller 30 with information as to the pressure within compensator 10. Sensor 47 provides controller 30 with the temperature within the compensator 10. Sensor 48 located near snorkel 17 provides controller 30 with the pressure within bag 8. A touch screen 34 enables user input to controller 30 and display of outputs to a user via the screen. RFID reader 35 reads RFID tags contained within a load to be processed and provides the ID to controller 30. Controller 30 may write to an RFID tag via RFID reader 35 also, if desired.

Storage device 36 provides, data storage for controller 30. Communications circuit 37 provides wire or wireless communications between controller 30 and an external computer. Controller 30 may control actuator 38 to raise and lower clamp 22a. Controller 30 may supply power to sealing bar 22b to seal a sterilisation bag. Controller 30 drives the elements 21a of heating plate 20 and 21b. Controller 30 may supply fluid from steam generator 29 which may supply steam to a bag 8 within compensator 10 via nozzle 17a. Controller 30 may also drive pump 40 so that vacuum venturi 41 removes fluid from compensator 10 and returns it to cold water tank 42. Vacuum venturi 41 may also remove steam from bag 8 to condenser 43 to supply hot water to hot water tank 46 be returned via water pump 39 to steam generator 29. Controller 30 also controls compressor 44 to pressurise compensator 10. Pressure is reduced in compensator 10 by actuating water pump 40 to drive vacuum venturi 41.

When the door 11 is closed, a start instruction is given to a controller 30 via touch screen 34. Prior to processing a load controller 30 may interrogate an RFID tag or other electronic identification device within a package, to see if it has a valid identification code. The identification code read by RFID reader is 35 supplied to controller 30 which may compare the code with its internal memory 36 or with a remote database via communications circuit 37. Controller 30 may allow further processing only if the identification code is a valid identification code. If valid the door seal 49 is actuated to seal the door and clamp 22a descends (from the rest position shown in FIG. 3) under control of ram 25, clamping the packaging 8 opening 7 around the intruding conduit 17a by compressing the packaging and conduit between the upper clamp 22a and lower clamp 14a. This effectively clamps the packaging about the snorkel 17 as shown in FIG. 3.

Figures 3, 4:
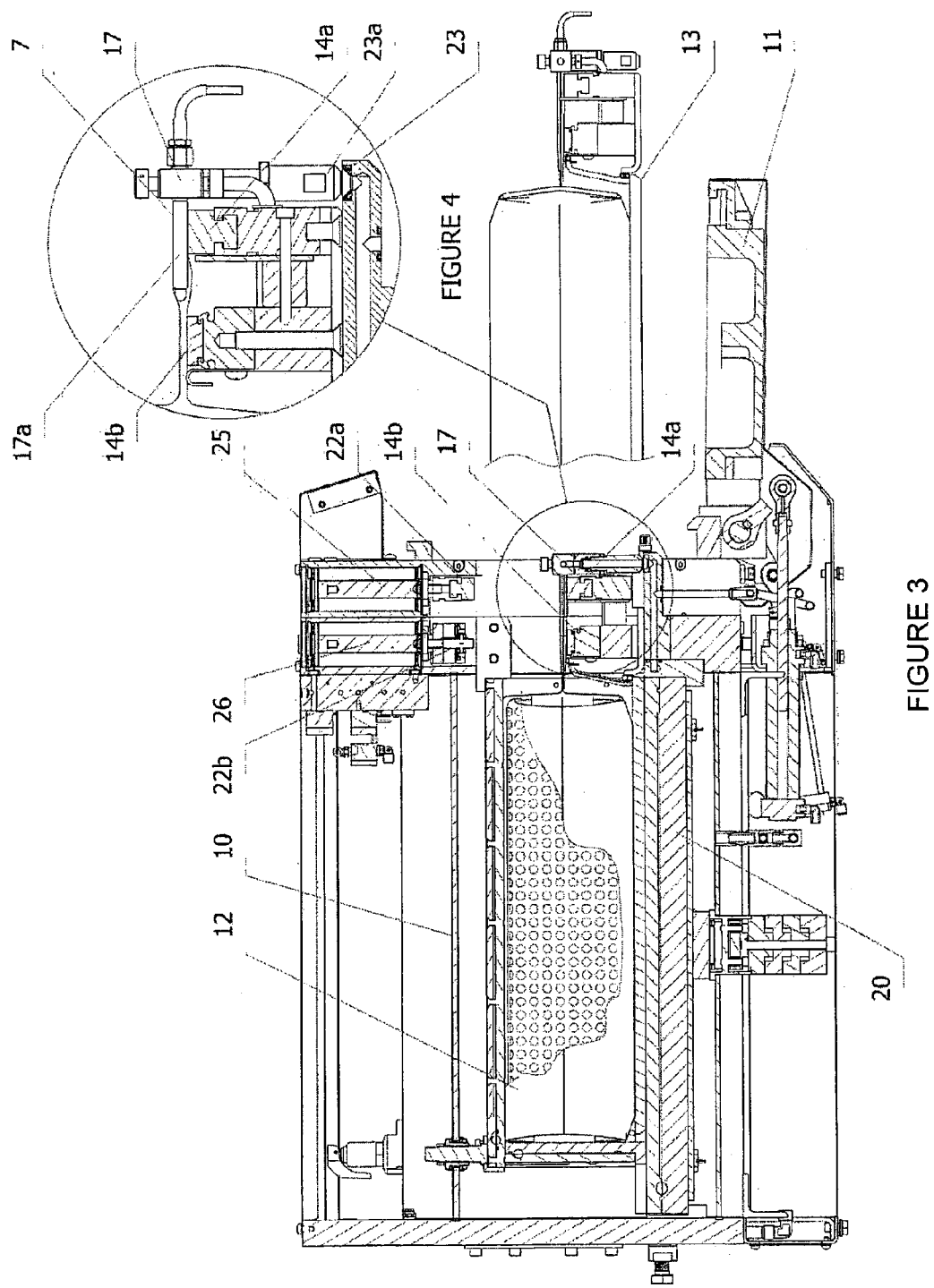
FIG. 3 is a cross-sectional elevation view of the apparatus shown in FIG. 1.
FIG. 4 is a more detailed view of the snorkel, clamping and sealing mechanism and services socket arrangement, but with the clamping and sealing mechanism shown in the rest position.

At the same time services are connected to the snorkel 17 via services supply socket 23 that mates with socket 23a of snorkel 17 as also shown in FIG. 4.

The processing basket 12 is located and held in position by the door 11 within the closed and interlocked compensator 10 when the start cycle instruction is given. Vacuum is then applied by actuating water pump 40 to remove, via vacuum venturi 41 and snorkel 17, air from within the packaging and load/items until the required amount of air has been removed. The cycle pauses to test for vacuum leaks and correct fitment of the packaging and clamp bar arrangement about the snorkel 17.

When a vacuum is applied to the interior of the sealable packaging 8 a deeper vacuum is simultaneously applied to the exterior of the packaging in the compensator 10 until the desired level of air removal within the package 8 and load has been achieved, as monitored by sensors 33 & 48. This ensures that the flexible sterilisation bag 8 does not collapse and restrict the flow of fluid within the bag and via the conduit 17a.

The sterilant is then injected via the snorkel 17 into the packaging 8 to sterilise the contents. Should the sterilant be steam, an external steam generator/boiler 29 provides steam to inside the packaging via the snorkel 17 as directed by the cycle process and additionally the heating plates 20 and 21b act to directly heat the condensate that has formed within the bottom of the packaging turning it back to steam and reducing the volume requirement for steam into the packaging (effectively recycling the condensate).

During the introduction of sterilant to the interior of the packaging 8 a counter pressure medium (in the preferable form of compressed air) is simultaneously introduced into compensator 10 by compressor 44 to increase the pressure in the compensator above atmospheric pressure (typically about 2 atmospheres) so as to stop the packaging 8 from blowing up under pressure and prevents seal stress/rupture of packaging 8. This also maximises contact with the heating plates 20 and 21b. The sides of the packaging 8 will be restrained and the combination of packaging and compressed air on the exterior of the packaging 8 will hold the steam pressure within the packaging 8 at the process temperature (usually 134 degrees. Celsius) until the predetermined sterilisation parameters have been fulfilled. Sensor 31 provides information as to, the temperature of steam supplied to, packaging 8 and sensor 48 provides information as to the pressure within the bag so that controller 30 can monitor sterilisation conditions and control operation accordingly.

The sterilant is then removed from the interior of package 8 by gradually applying a vacuum to the interior of the package 8 to evacuate the sterilant/steam and facilitate drying of the load, whilst simultaneously applying a vacuum to the exterior of the package 8 during this phase to minimise and control the vacuum crush effect on the load in the package 8. Vacuum is applied by driving pump 40 by which via vacuum venturi 41 evacuates compensator 10 and the interior of bag 8 (via condenser 43) whilst maintaining a heated compensating pressure to the exterior of the packaging by means of the heating plate 20 and heating source 21b to ensure thorough drying of the interior of the bag and items to be sterilised (the load).

Finally as a possible embodiment a drying medium, such as dry, filtered air 45 or superheated steam, may be introduced into the packaging 8 to dry items in the packaging whilst the vacuum is simultaneously controlled on the exterior of the package 8 in the compensator 10.

Finally a vacuum may be applied and the packaging 8 sealed while under partial vacuum via the seal bar 22b. The upper seal bar 22b contains the sealing element which heat seals the packaging 8 just behind the clamp 14a, 14b and conduit 17a by compressing (via further operation of cylinder 26) the seal bar 22b down on to the lower seal anvil 14b. The package is thus sealed, following which the seal bar 22b and clamp bar 22a are returned to the raised open position (FIG. 4), the compensator 10 is returned to atmospheric pressure and the door 11 interlock released. The compensator 10 can thus be opened and the sterilised packaging 8 is presented for removal. Due to the vacuum sealing it will be immediately obvious if the packaging integrity is intact by visual inspection when a user comes to use the vacuum sealed packaging (i.e. the packaging should be forced tightly against cage 12).

Figure 11:
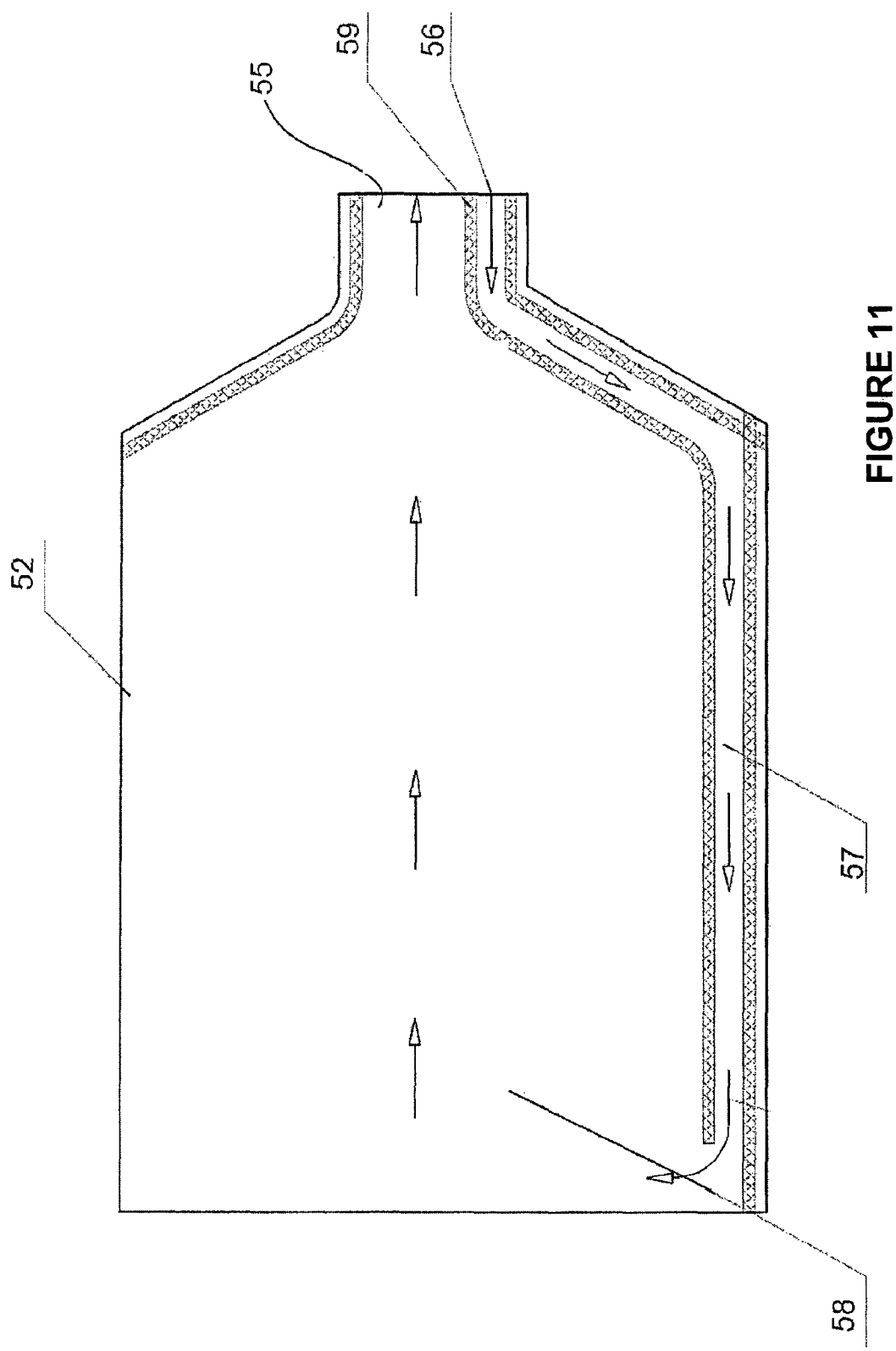
FIG. 11 shows a bag utilised in the embodiment shown in FIGS. 8 to 10.
Figure 12:
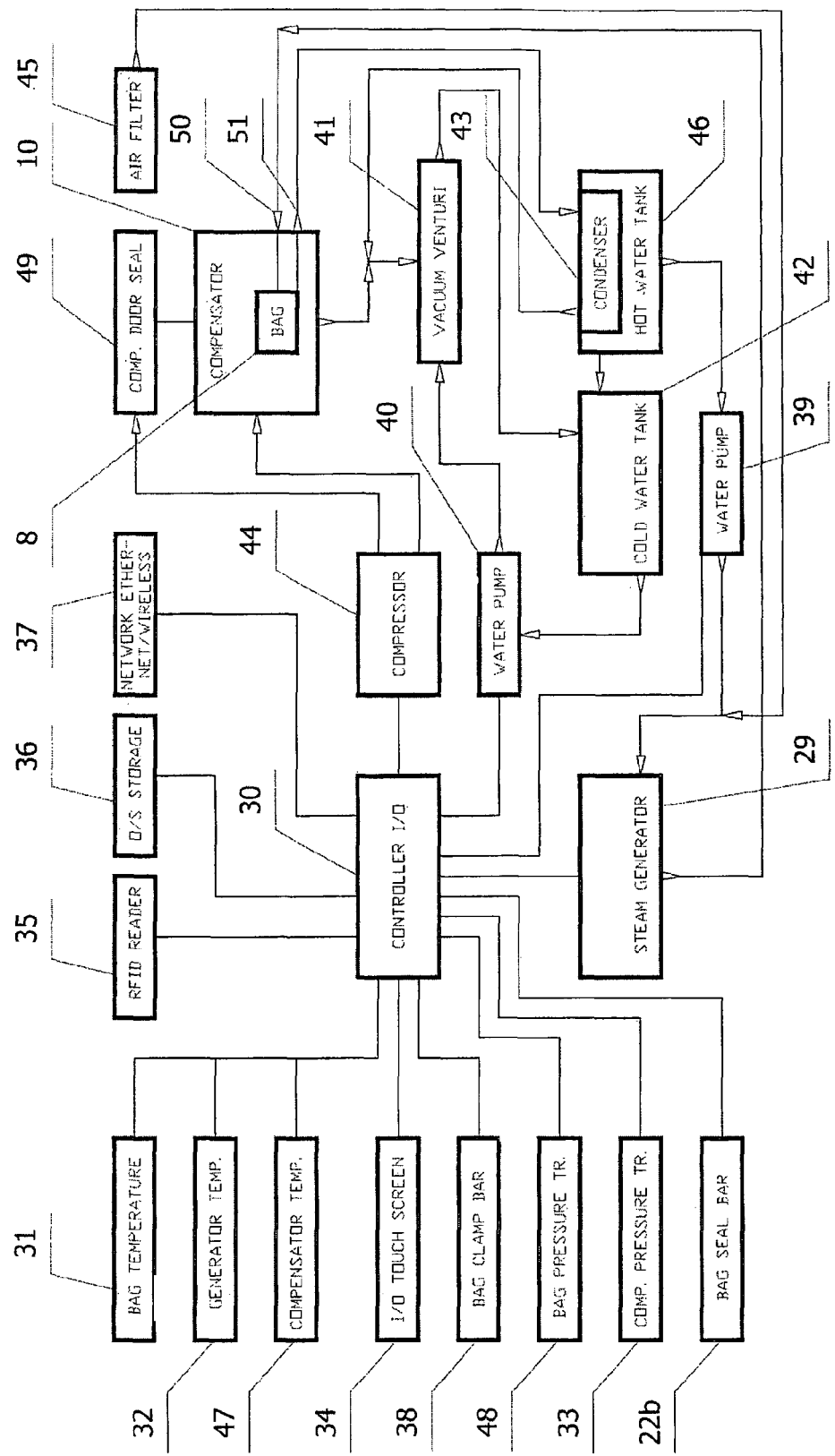
FIG. 12 shows a schematic diagram of the electric and fluid system of the embodiment shown in FIGS. 8 to 11.

Referring now to FIGS. 8 to 12 an alternative embodiment is shown in which the snorkel 53 has dual nozzles 50 and 51 to allow the circulation of filtered air or superheated steam within bag 52. Like elements to those shown in FIGS. 1 to 7 have been given the same numbering. The modified embodiment is shown in FIGS. 8 to 12 utilises dual nozzles 50 and 51, the bag construction shown in FIG. 11 and a different fluid flow arrangement as shown in FIG. 12. Dual nozzles 50 and 51 are employed in this embodiment to facilitate improved drying of the load prior to sealing. The bag shown in FIG. 11 is divided into a channel 57 and a bag interior 58 by fusing the walls of the bags together by heat sealing along line 59. Inlet nozzle 51 engages with opening 56 to supply fluid to channel 57. This is introduced to the interior of the bag 58, circulated through the bag then removed via opening 55 which engages the nozzle 50.

Operation is as per the previous embodiment except that during the drying stage either heated air from air filter 45 is heated and supplied via nozzle 51 to opening 56 or steam vapour is removed from bag via a fan/pump so that super heated steam is supplied by nozzle 51 to opening 56. With heated air—a vacuum is applied to opening 55 via nozzle 50 with extracted fluid condensed by condenser 43. This embodiment offers improved drying due to the circulation of fluid within the bag.

The apparatus capacity is expected to be designed along the capacities consisting of Sterile Units (StU), either in portions or multiples thereof from small dental units to large 'banks' of apparatus with each individual apparatus incorporating all its services (vacuum, steam) and controller.

It is feasible that a single computer controller could manage a bank of the sterilising apparatus 9 to replace the traditional multi-load sterilisers in use today. This means that individual items or loads could be prioritised to suit production/user requirements. The potential to incorporate automated loading and unloading systems is also envisaged due to the versatility of the invention.

The package 8 will need to be made to required specifications, specific to this application. The package (and film) will be impervious and non-porous to facilitate the parameters of steam sterilisation and be able to hold a vacuum for a prolonged period under sealed conditions. Means may be incorporated in the package 8 and apparatus 9 to enable the apparatus 9 to either accept or reject a package 8, through a process of authentication and/or unique number marking.

The package 8 and basket 12 in conjunction with the apparatus 9 may incorporate a unique number marking system and/or radio frequency identification system (RFID) to facilitate data capture at tray 12 level of sterilisation parameters and facilitate full tracking and traceability with other software systems.

The instrument basket and lid 12 & 12a will preferably be constructed of stainless steel mesh or aluminium or suitable substitute material. As disclosed above the basket and lid 12/12a will contain the items and maintain the packages shape around the carrier under vacuum thereby preventing damage or puncturing of the package's wall integrity from the internal items to be sterilised. The basket 12 may be fitted with an insert or adjustable/variable clamp/partitioning to best accommodate the items.

Controller 30 may incorporate control hardware and software that enables real time control of the process parameters irrespective of the load configuration. The benefit of real time control, monitoring and data capture of sterilisation parameters in the interior of the package 8 at individual tray level is that the validation of cycle parameters versus load variability will no longer be a challenge.

The apparatus 9 may be fitted with a printer to print the cycle parameters and all other relevant data as deemed necessary. This will result in a number of process, logistic; materials handling, tracking and quality control benefits. Thus data may also be written to an RFID tad within packaging 8 or communicated via communication circuit 37 to a remote database.

The packaging 8 and basket 12/12a may preferably accommodate a clearly visible sterilisation monitoring device or indicator within the packaging 8 to indicate the status of the load and independently confirm whether the items/load is sterile or not.

The combination of apparatus 9, package 8 and process of the invention provides an inventive new method to achieve sterilisation more efficiently with numerous operational and clinical benefits.

The design incorporates energy efficiencies resulting in substantially reduced power and sterilant usage with shorter overall cycle times. Based on the international standard sterile unit size(s), the package 8 is loaded via the standardised processing basket 13 thereby facilitating and promoting standardisation of individual load dynamics.

The ergonomics of the apparatus 9, stand-alone design incorporating all the services (vacuum, steam generator, pure water reservoir, automatic controller etc.) and relative small footprint facilitates substantial floor space, operational and capital expenditure savings. The front loading or optional pass-through double ended design allows a seamless integration with modern appliance fitments.

The apparatus 9 and package 8 offer a means to replace the challenges presented by existing packaging practices and/or storage containers and offers extended product shelf life with immediate visible indication of contamination or barrier failure. This process offers a substantially quicker full sterilisation processing time opening numerous opportunities for quick processing of items requiring a short turnaround time. In addition the apparatus does not require a large inefficient pressure vessel and associated steam generator therefore offering substantial total cost of ownership benefits and reduces the impact on the environment.

The sterilisation medium or sterilant is not limited to steam only as the principles incorporated in, the invention can be universally applicable to other mediums currently used in low temperature sterilisers.

A further modification is that rather than vacuum seal the packaging the packaging could be bought back to atmospheric pressure and sealed. Other possibilities are to pressurise or gas flush the packaging and then seal the packaging.

The apparatus shall not be limited to the preferred embodiment and may take the form of a top loader, double ended pass through or auto loading device, or multiples of the apparatus. In the preferred embodiment the apparatus shall process a single load and shall not be limited to the preferred embodiment and may take the form of processing multiple loads in a single apparatus.

The invention as described herein is open to modification as will be appreciated by those skilled in the art. For example, rather than perform as a steriliser the apparatus could be used as a retort or food cooking apparatus but not limited to only these applications.

Other modifications and improvements to the invention will be apparent to the skilled person and will fall within the scope of the invention as it is intended.

It is believed that the process described overcomes most shortcomings of current practices and procedures due to the fact that the load is placed into the sealable non-porous, impervious package for the duration of the complete sterilisation process and then the impervious packaged is hermetically sealed. The vacuum packed terminally sterile load remains safely within the non-porous impervious package offering viral and liquid barrier protection. Therefore the probability of recontamination is minimised whilst the package seal integrity is maintained.

The combination of an innovative apparatus and sealable package in effect replaces the necessity for an inefficient conventional steriliser and breathable barrier technologies.

Due to the process of sterilisation occurring within the confines of the package in direct contact with the load, not a large spacious chamber containing the load(s) plus the unutilised chamber volume, the resultant services (steam/vacuum) requirements are significantly reduced thereby offering increased processing efficiencies and vastly improved direct control.

Use of a pressure compensating compartment minimises the demands placed on the package with respect to design, film, seal strength and clamp pressure around the mouth and snorkel and by ensuring a marginally lower pressure on the exterior of the package during the sterilant phase resulting in a package under positive pressure thereby reducing the possibility of non-sterile ingression from the exterior similarly during the vacuum phase(s) a deeper vacuum is pulled on the exterior of the package than within the interior of the package reducing the possibility of non-sterile ingression.

Vacuum sealing the sterilisation bag under vacuum at the end of the sterilisation process results in an impervious non-porous package offering a pre-determined shelf life and immediate visible means of detection should the package seal be compromised.

The use of identification features allows bag validation and the stopping of the sterilisation process should there be a failure at any stage. The use of a unique identification code for each bag allows bag authentication and traceability at tray level as well as recordal of each stage of the sterilisation process for a specific load.

The process of the present invention will remove air from directly inside the packaging within seconds/minutes whilst pre-heating the load, sterilisation parameters of pressure and time will adhere to international recognised standards (typically 3.5-5 minutes @ 134 degrees Celsius of steam penetration to facilitate sterilisation) followed by the drying phase by means of removing the majority of the steam/condensate through pulling a vacuum in the package whilst the package is located within the heating plates, drying will be facilitated within minutes. It is envisaged that most sterilisation cycle time(s) may be reduced by more than 50%, subject to the load mass.

The sterilised load (items) will be vacuum sealed in the packaging at the end of the sterilisation cycle and it is believed that the invention will result in less likelihood of wet load problems due to direct heat transfer of heat from the heating plate during the drying phase. Nevertheless due to non-use of wrap (or optional inner very porous wrap purely for enhancement of aseptic release) vacuum drying efficiency will be greatly enhanced, notwithstanding this fact there will be no requirement for the load to be completely dry as the packaging barrier ensuring sterility retention will be impervious and non-porous. The shelf life of a sterile load(s) shall be controllable, monitor friendly and possibly significantly extended and may very well be indefinite.

It is anticipated that the method of sterilisation according to the invention will provide substantial efficiencies and cost savings in the sterilisation process model. The process of the present invention will remove air from directly inside the packaging within seconds/minutes whilst pre-heating the load, sterilisation parameters of pressure and time will adhere to international recognised standards (typically 3.5-5 minutes @ 134 degrees Celsius of steam penetration to facilitate sterilisation) followed by the drying phase by means of removing the majority of the steam/condensate through pulling a vacuum in the package whilst the package is located on the heating plate, drying will be facilitated within minutes. It is envisaged that most sterilisation cycle time(s) may be reduced by more than 50%, subject to the load mass.

While the present invention has been illustrated by the description of the embodiments thereof, and while the embodiments have been described in detail, it is not the intention of the Applicant to restrict or in any way limit the scope of the appended claims to such detail. Additional advantages and modifications will readily appear to those skilled in the art. Therefore, the invention in its broader aspects is not limited to the specific details, representative apparatus and method, and illustrative examples shown and described. Accordingly, departures may be made from such details without departure from the spirit or scope of the Applicant's general inventive concept.

The invention claimed is:

1. A method of sterilizing items including the steps of:
   a. placing items to be sterilised sterilized into a puncture resistant sealable vapor barrier sterilization bag;
   b. performing steam sterilisation under pressure via a conduit coupled to the bag;
   c. monitoring the pressures internal and external to the sterilization bag and maintaining a compensating pressure environment around the exterior of the bag during steam sterilization based on the internal and external pressures so as to reduce mechanical stress on the bag; and
   d. sealing the bag at the completion of sterilization.

2. A method as claimed in claim 1 wherein after placing the items into the bag, the bag is sealed so as to leave only an opening suitable for sealingly coupling with the conduit.

3. A method as claimed in claim 1 wherein the bag is evacuated prior to steam sterilization and the pressure around the bag is reduced below atmospheric pressure during evacuation so as to facilitate effective evacuation of the bag.

4. A method as claimed in claim 1 wherein steam sterilization is performed within the bag at above atmospheric pressure and the pressure around the bag is maintained above atmospheric pressure during steam sterilization so as to reduce mechanical stress on the bag.

5. A method as claimed in claim 1 wherein the bag is maintained in a pressure compensating compartment during sterilization.

6. A method as claimed in claim 5 wherein the bag is sealed after sterilization and drying within the pressure compensating compartment before the pressure compensating compartment is opened.

7. A method as claimed in claim 6 wherein the bag is heat sealed.

8. A method as claimed in claim 1 wherein the interior of the bag and items within the bag are dried during the evacuation of the sterilant from within the bag after the sterilization cycle.

9. A method as claimed in claim 8 wherein the exterior of the inflated bag is maintained in contact with heated surfaces during the sterilization and drying cycle to facilitate drying of the interior of the bag and items to be sterilized.

10. A method as claimed in claim 1 wherein a drying fluid is introduced via an opening in the bag, circulated within the bag and removed from the bag to facilitate drying of items in the bag.

11. A sterilization services apparatus for sterilizing the contents of a sterilization bag including:
   a. a pressure compensating compartment having a sealable door;

b. a bag pressure sensor which monitors the pressure within the sterilization bag;

c. a pressure compensating compartment pressure sensor which monitors the pressure within the compensating compartment;

d. a fluid conduit adapted to couple to an opening of a sterilization bag during sterilization within the pressure compensating compartment;

e. a steam generator to supply steam to the bag via the conduit;

f. a bag sealing unit to seal the opening of the sterilization bag g. a vacuum pump for evacuating a sterilization bag via the conduit prior to steam sterilization; and h. a controller which controls the supply of fluid to or from the pressure compensating compartment based on the pressure sensed by the bag pressure sensor and pressure compensating compartment pressure sensor to maintain a compensating pressure environment around the exterior of the sterilization bag during steam sterilization and drying so as to reduce mechanical stress on the bag.

12. A sterilization services apparatus as claimed in claim 11 including a pair of fluid conduits adapted to couple with one or more openings of the sterilization bag to facilitate the circulation of fluid in via one conduit and out via another.

13. A sterilization services apparatus as claimed in claim 12 wherein heated air is supplied to facilitate drying of the load within the sterilization bag.

14. A sterilization services apparatus as claimed in claim 11 including a clamp to form a sealed connection between the conduit and an opening of a sterilization bag by applying a clamping pressure thereto.

15. A sterilization services apparatus as claimed in claim 11 including a heat sealing bar and anvil to heat seal the bag in front of the conduit coupling.

* * * * *